United States Patent [19]
Büchel et al.

[11] 3,972,892
[45] Aug. 3, 1976

[54] 1-[1,2,4-TRIAZOLYL-(1)]-2-ARYLOXY-3-HYDROXY-ALKANES

[75] Inventors: Karl Heinz Büchel; Wolfgang Krämer, both of Wuppertal; Helmut Kaspers, Leverkusen; Wilhelm Brandes, Cologne, all of Germany

[73] Assignee: Bayer Aktiengesellschaft, Leverkusen, Germany

[22] Filed: Sept. 27, 1974

[21] Appl. No.: 509,881

[30] Foreign Application Priority Data
Oct. 5, 1973 Germany............................ 2350122

[52] U.S. Cl............................. 260/308 R; 424/269
[51] Int. Cl.². ..................................... C07D 249/08
[58] Field of Search ............................... 260/308 R Primary Examiner—Richard J. Gallagher
Attorney, Agent, or Firm—Burgess, Dinklage & Sprung

[57] ABSTRACT

1-[1,2,4-triazolyl-(1)]-2-aryloxy-3-hydroxyalkanes of the formula

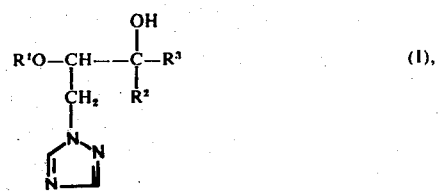

in which
R$^1$ is optionally substituted aryl,
R$^2$ is hydrogen, alkyl, alkenyl, cycloalkyl, optionally substituted aryl or optionally substituted aralkyl, and
R$^3$ is alkyl or cycloalkyl, or can be hydrogen if R$^2$ does not denote hydrogen,
which possess fungicidal properties.

5 Claims, No Drawings

1-[1,2,4-TRIAZOLYL-(1)]-2-ARYLOXY-3-HYDROXY-ALKANES

The present invention relates to and has for its objects the provision of particular new 1-[1,2,4-triazolyl-(1)]-2-aryloxy-3-hydroxy-alkanes, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in German Published Specification DOS 1,795,249 that trityl-triazoles, such as triphenyl-1,2,4-triazolyl-(1)-methane (Compound A), exhibit good fungicidal activity. However, their action is not always entirely satisfactory, especially when they are used in low amounts and low concentrations to combat fungal diseases of cereals. Furthermore, it is known from Phytopathology, Vol. 33 (1963) p. 1113 that zinc ethylene-1,2-bis-dithiocarbamate is a good agent for combating fungal diseases of plants. However, its use as a seed dressing is subject to limitations since it only has a slight activity when low amounts and low concentrations are used.

The present invention provides, as new compounds, the 1-propyl-1,2,4-triazolyl derivatives of the general formula

in which
R$^1$ is optionally substituted aryl,
R$^2$ is hydrogen, alkyl, alkenyl, cycloalkyl, optionally substituted aryl or optionally substituted aralkyl, and
R$^3$ is alkyl or cycloalkyl, or can be hydrogen if R$^2$ does not denote hydrogen,
and their salts.

Surprisingly, the active compounds according to the invention exhibit a substantially greater fungicidal action than the known compound triphenyl-1,2,4-triazolyl-(1)-methane (A), which is chemically the nearest active compound. The active compounds according to the present invention thus represent an enrichment of the art.

Preferably, R$^1$ is optionally monosubstituted or polysubstituted aryl with 6 to 10 carbon atoms, especially with 6 carbon atoms, preferred substituents being halogen, especially fluorine, chlorine or bromine, straight-chain or branched alkyl with 1 to 6, especially 1 to 4, carbon atoms, alkoxy, alkylthio and alkylsulfonyl with 1 to 4, especially 1 or 2, carbon atoms, halogenoalkyl with 1 or 2 carbon atoms and 1 to 5 halogen atoms, especially fluorine and chlorine, halogenoalkoxy and halogenoalkylthio with 1 or 2 carbon atoms and 3 to 5 halogen atoms, especially fluorine and chlorine, for example chlorodifluoromethylthio and chlorodifluoromethoxy, alkoxycarbonyl with 1 to 4 carbon atoms in the alkoxy moiety, phenyl in the o- or p-position, amino and nitro; R$^2$ is hydrogen, alkyl with up to 6, especially up to 4, carbon atoms, optionally substituted aryl with 6 to 10 carbon atoms or aralkyl with 6 to 10 carbon atoms in the aryl moiety which may be substituted, and 1 or 2 carbon atoms in the alkyl moiety, the preferred substituents on the aryl radicals being fluorine, chlorine, alkyl with up to 4 carbon atoms and alkoxy with up to 4 carbon atoms; and R$^3$ is straight chain or branched alkyl with 1 to 6, especially 1 to 4, carbon atoms, or cycloalkyl with 5 to 7, especially 5 or 6 carbon atoms, or can be hydrogen if R$^2$ does not denote hydrogen.

The compounds of the formula (I) possess two asymetrical carbon atoms and can therefore exist in the erythro form and in the threo form; in both cases, they are obtained predominantly as racemates.

The present invention also provides a process for the preparation of a compound of the present invention in which an ethyl-triazole of the general formula

in which
R$^1$ and R$^3$ have the above-mentioned meanings,
a. is reduced with hydrogen in the presence of a catalyst and optionally in the presence of a polar solvent, or
b. is reduced with aluminum isopropylate in the presence of a solvent, or
c. is reduced with a complex hydride, optionally in the presence of a polar solvent, or
d. is reduced with formamidinesulfinic acid and an alkali metal hydroxide, optionally in the presence of a polar solvent, or
e. is reacted with an organo-metallic compound of the general formula

in which
R$^4$ is alkyl, alkenyl, cycloalkyl, optionally substituted aryl or optionally substituted aralkyl, and
M is an alkali metal or the radical X-Mg wherein X is chlorine, bromine or iodine,
in the presence of an inert solvent, the 1-propyl-1,2,4-triazolyl prepared in any of the process variants (a) – (e) being converted, if required, into a salt thereof.

If 1-[1,2,4-triazolyl-(1)]-2-(p-chlorophenoxy)-4,4-dimethyl-pentan-3-one and hydrogen are used as starting compounds in process variant (a), the course of the reaction can be represented by the following equation:

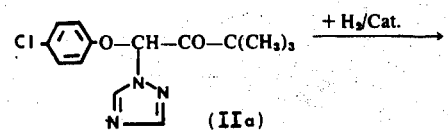

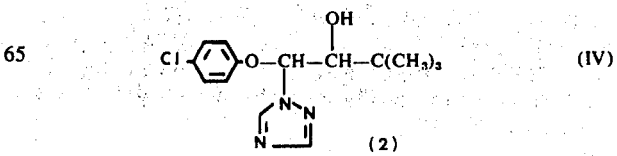

If 1-[1,2,4-triazolyl-(1)]-2-(p-chlorophenoxy)-4,4-dimethyl-pentan-3-one and aluminum isopropylate are used as the starting compounds in process variant (b), the course of the reaction can be represented by the following equation:

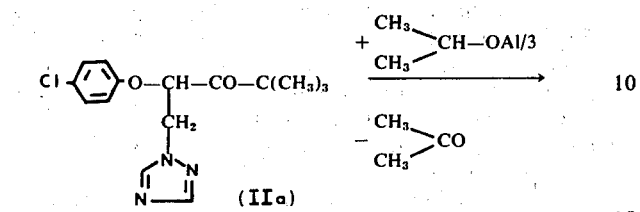

If 1-[1,2,4-triazolyl-(1)]-2-(p-chlorophenoxy)-4,4-dimethyl-pentan-3-one and sodium borohydride are used as starting compounds in process variant (c), the course of the reaction can be represented by the following equation:

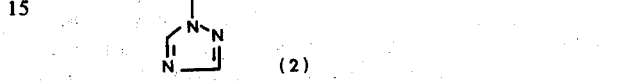

If 1-[1,2,4-triazolyl-(1)]-2-(p-chlorophenoxy)-4,4-dimethyl-pentan-3-one and formamidinesulfinic acid are used as starting compounds in process variant (d), the course of the reaction can be represented by the following equation:

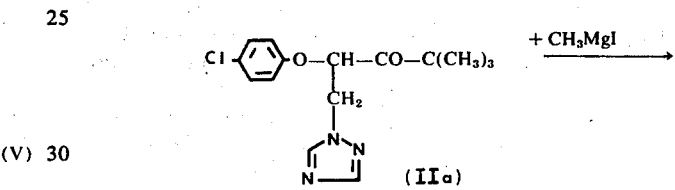

If 1-[1,2,4-triazolyl-(1)]-2-(p-chlorophenoxy)-4,4-dimethyl-pentan-3-one and methyl-magnesium iodide are used as starting compounds in process variant (e), the course of the reaction can be represented by the following equation:

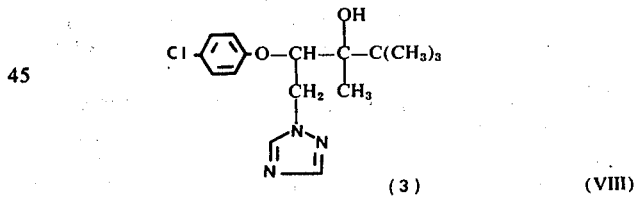
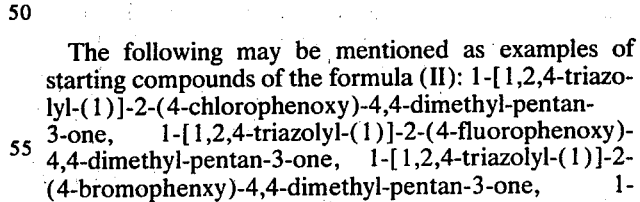

The following may be mentioned as examples of starting compounds of the formula (II): 1-[1,2,4-triazolyl-(1)]-2-(4-chlorophenoxy)-4,4-dimethyl-pentan-3-one, 1-[1,2,4-triazolyl-(1)]-2-(4-fluorophenoxy)-4,4-dimethyl-pentan-3-one, 1-[1,2,4-triazolyl-(1)]-2-(4-bromophenxy)-4,4-dimethyl-pentan-3-one, 1-[1,2,4-triazolyl-(1)]-2-phenoxy-4,4-dimethyl-pentan-3-one, 1-[1,2,4-triazolyl-(1)]-2-(2-diphenoxy)-4,4-dimethyl-pentan-3-one, 1-[1,2,4-triazolyl-(1)]-2-(4-diphenoxy)-4,4-dimethyl-pentan-3-one, 1-[1,2,4-triazolyl-(1)]-2-(2-methylphenoxy)-4,4-dimethyl-pentan-3-one, 1-[1,2,4-triazolyl-(1)]-2-(2,3-dimethylphenoxy)-4,4-dimethyl-pentan-3-one, 1-[1,2,4-triazolyl-(1)]-2-(3,4-dimethylphenoxy)-4,4-dimethyl-pentan-3-one, 1-[1,2,4-triazolyl-(1)]-2-(2,4-dimethylphenoxy)-4,4-dimethyl-pentan-3-one, 1-[1,2,4-triazolyl-(1)]-2-(2,5-dimethylphenoxy)-4,4-dimethyl-pentan-3-one, 1-[1,2,4-triazolyl-(1)]-2-(2,6-dimethylphenoxy)-4,4-dimethyl-pentan-3-one, 1-[1,2,4-triazolyl-(1)]-2-(3,4,5-trichlorophenoxy)-4,4-dimethyl-pentan-3-one, 1-[1,2,4-triazolyl-(1)]-2-(3-trifluoromethylphenoxy)-4,4-dimethyl-pentan-3-one, 1-[1,2,4-triazolyl-(1)]-2-(4-trifluoromethylphenoxy)-4,4-dimethyl-pentan-3-one, 1-[1,2,4-triazolyl-(1)]-2-(2-trifluoromethylphenoxy)-4,4-dimethyl-pentan-3-one, 1-[1,2,4-triazolyl-(1)]-2-(2,5-dichlorophenoxy)-4,4-dimethyl-pentan-3-one and 1-[1,2,4-triazolyl-(1)]-2-(2,4-dichlorophenoxy)-4,4-dimethyl-pentan-3-one.

The ethyl-triazoles of the formula (II) which can be used according to the invention have not previously been described in the literature. They can be prepared according to the process described in application Ser. No. 483,758, filed June 27, 1974, now pending, the disclosure of which is incorporated herein by reference, by reacting alkyl-(1-aryloxy-2-halogenoethyl)-ketones (or corresponding aldehydes) with 1,2,4-triazole, optionally in the presence of a polar solvent and of an acid-binding agent, at temperatures of 50° to 150°C. The compounds of the formula (II) are isolated, and purified, in the usual manner.

The alkyl-(1-aryloxy-2-halogenoethyl)-ketones required as starting compounds have also not been previously described in the literature but can be prepared according to methods which are generally customary. For example, such a compound is obtained by condensing a phenol or naphthol with an alkylhalogenomethylketone in a manner which is in itself known and reacting the resulting alkyl-aryloxymethyl-ketone, in accordance with customary methods, with formaldehyde or a formaldehyde donor, for example a 40% strength aqueous formaldehyde solution, in an inert organic solvent, for example ethanol, in the presence of alkali, for example aqueous sodium hydroxide solution, at an elevated temperature, for example the boiling point of the reaction mixture, isolating the desired product in the usual manner and purifying it, or by subsequently treating the resulting alkyl-(1-aryloxy-2-hydroxy-ethyl)-ketone, without isolating it, with a halogenating agent, for example thionyl chloride, in an inert polar organic solvent, for example methylene chloride, at room temperature. The compounds are isolated and purified according to customary methods, as illustrated hereinbelow.

Preferred salts of the compounds of the formula (I) are salts with physiologically tolerated acids, especially the hydrogen halide acids such as, for example, hydrobromic acid and, more especially, hydrochloric acid, phosphoric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and 1,5-naphthalenedisulfonic acid.

Possible diluents for the reaction in accordance with process variant (a) are polar organic solvents, especially alcohols, such as methanol and ethanol, and nitriles, such as acetonitrile. The reaction is carried out in the presence of a catalyst. Preferably, noble metal catalysts, noble metal oxide catalysts or noble metal hydroxide catalysts or so-called "Raney catalysts" are used, especially platinum, platinum oxide and nickel. The reaction temperatures can be varied over a fairly wide range. In general, the reaction is carried out at between 20° and 50°C, preferably at between about 20° and 40°C. The reaction can be carried out not only under normal pressure but also under elevated pressure, e.g., 1 to 2 atmospheres gauge. In the reaction according to process variant (a), about 1 mole of hydrogen and about 0.1 mole of catalyst are generally employed per mole of the compound of the formula (II); to isolate the product, the catalyst is filtered off, the solvent is removed in vacuo and the resulting compound of the formula (I) is purified by recrystallization. If desired, a salt of the compound according to the invention may be obtained according to any customary method.

If process variant (b) is employed, preferred diluents for the reaction are alcohols, such as isopropanol, and inert hydrocarbons, such as benzene. The reaction temperatures can again be varied over a fairly wide range; in general, the reaction is carried out at between 20° and 120°C, preferably about 50° to 100°C. To carry out the reaction, about 1 to 2 moles of aluminum isopropylate are generally employed per mole of the compound of the formula (II). To isolate the compound of the formula (I), the excess solvent is removed by distillation in vacuo and the resulting aluminum compound is decomposed with dilute sulfuric acid or sodium hydroxide solution. The further working up is carried out in the usual manner.

If process variant (c) is employed, possible diluents for the reaction according to the invention are polar organic solvents, especially alcohols, such as methanol, ethanol, butanol and isopropanol, and ethers, such as diethyl ether or tetrahydrofuran. The reaction is generally carried out at from 0° to 30°C, preferably at about 0° to 20°C. About 1 mole of a complex hydride, such as sodium borohydride or lithium alanate, is employed per mole of the compound of the formula (II). To isolate the compound of the formula (I), the residue is taken up in dilute hydrochloric acid and the mixture is then rendered alkaline and extracted with an organic solvent. The further working up is carried out in the usual manner.

Possible diluents for the reaction in accordance with process variant (d) are polar oganic solvents, preferably alcohols, such as methanol and ethanol, and also water. Here again, the reaction temperatures can be varied over a fairly wide range; the reaction is generally carried out at temperatures between 20° and 100°C, preferably at about 50° to 100°C. To carry out the reaction, about 1 to 3 moles of formamidinesulfinic acid and 2 to 3 moles of alkali metal hydroxide are generally employed per mole of the compound of the formula (II). To isolate the end product, the reaction mixture is freed from the solvent and the residue is extracted with water and organic solvents, worked up in the usual manner and purified; a salt thereof is prepared if desired.

In the reaction according to process variant (e), a compound of the general formula (I) is obtained in which $R^2$ does not represent hydrogen. In contrast, the reactions according to (a) to (d) are reduction reactions; the compounds of the formula (I) thereby obtained are secondary alcohols in which $R^2$ in each case only represents hydrogen.

M in the formula (III) is preferably lithium, sodium or a so-called "Grignard grouping" Mg-X, wherein X represents chlorine, bromine and iodine. Organo-metallic compounds of the formula (III) are known; a summary and survey of numerous disclosures are to be found, for example, in G. E. Coates "Organo-Metallic Compounds", 2nd edition, Methuen and Co., London (1960).

For the reaction according to process variant (e), anhydrous ethers, such as diethyl ether, dibutyl ether and cyclic ethers, such as tetrahydrofuran, are preferably employed. The reaction temperatures can be varied between about 0° and 80°C, preferably between about 30° and 60°C. In carrying out process variant (e), about 1 mole of the organo-metallic compound of the formula (III) is generally employed per mole of the compound of the formula (II). The mixtures obtained by organo-metallic reactions are worked up in the customary and generally known manner.

The active compounds according to the invention exhibit a powerful fungitoxic action. They do not harm crop plants in the concentrations required to combat fungi. For these reasons, they are suitable for use as plant protection agents for combating fungi. Fungitoxic agents are employed in plant protection for combating Archimycetes, Phycomycetes, Ascomycetes, Basidiomycetes and *Fungi Imperfecti.*

The active compounds according to the invention have a very broad spectrum of action and can be used against parasitic fungi which attack above-ground parts of plants, or attack the plants through the soil, and against seedborne pathogens.

They exhibit a particularly good action against parasitic fungi on above-ground parts of plants, such as species of Erysiphe, species of Podosphaera, and species of Venturia, and also against species of Piricularia and Pellicularia.

It should be emphasized that the active compounds according to the invention not only exhibit a protective action but are also curatively active, that is to say they can also be employed after the infection has occurred. Furthermore, the systemic action of the compounds should be pointed out. Thus it is possible to protect plants against fungal attack by supplying the active compound to the above-ground parts of plants through the soil, through the plant or through the seed. When used as plant protection agents, the active compounds according to the invention can be used for the treatment of seed and for the treatment of above-ground parts of plants.

The compounds according to the invention are well tolerated by plants. They have only a low toxicity towards warm-blooded animals and because of their slight odor and good toleration by human skin they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents.

The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. higher dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, rodenticides, bactericides, nematocides, herbicides, fertilizers, growth-regulating agents, bird repellents, plant nutrients, agents for improving the soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the concentrations of active compound in the use forms can be varied within a fairly wide range. The concentrations are generally between 0.1 and 0.00001 per cent by weight, preferably between 0.05 and 0.0001 per cent.

In the treatment of seed, amounts of active compound of 0.001 to 50 g, preferably 0.01 to 10 g, are generally required per kilogram of seed.

Furthermore, the present invention contemplates methods of selectively killing, combating or controlling pests, e.g. fungi, which comprises applying to at least one of correspondinly (a) scuh fungi, and (b) the corresponding habitat thereof, i.e. the locus to be protected, e.g. to a growing crop, to an area where a crop is to be grown or to a domestic animal, a correspondingly combative or toxic amount, i.e. fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1:

Erysiphe test

Solvent: 4.7 parts by weight of acetone
Emulsifier: 0.3 part by weight of alkylaryl polyglycol ether
Water: 95 parts by weight.

The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23°–24°C and at a relative atmospheric humidity of about 75%.

After 12 days, the infection of the cucumber plants was determined as a percentage of the untreated but also inoculated control plants. 0% means no infection; 100% that the infection was exactly as great as in the case of the control plants.

The active compounds, the concentrations of the active compounds and the results can be seen from the following table.

Table 1

Erysiphe test

| Active compound | Infection in % of the infection of the untreated control at an active compound concentration of 0.00025% |
|---|---|
| 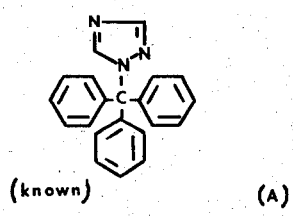 (known) (A) | 41 |
| 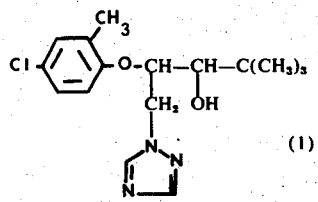 (1) | 2 |

EXAMPLE 2

Erysiphe test/systemic

Solvent: 4.7 parts by weight of acetone
Dispersing agent: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated additives.

Cucumber plants grown in standard soil, in the 1–2 leaf stage, were watered once within one week with 20 ml of the watering liquid, of the stated concentration of active compound, per 100 ml of soil.

The plants treated in this way were inoculated, after treatment, with conidia of the fungus *Erysiphe cichoracearum*. The plants were then set up in a greenhouse at 23°–24°C and 70% relative atmospheric humidity. After 12 days, the infection of the cucumber plants was determined as a percentage of the untreated, but also inoculated, control plants.

0% denotes no infection and 100% denotes that the infection was exactly as great as in the case of the control plants.

The active compounds, active compound concentrations and results can be seen from the table which follows:

Table B

Erysiphe test/systemic

| Active compound | Infection in % of the infection of the untreated control at an active compound concentration of 100 ppm |
|---|---|
| 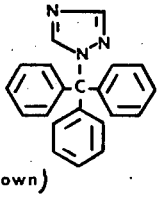 (known) (A) | 91 |
| 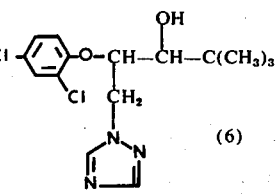 (6) | 0 |
| 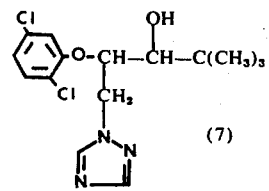 (7) | 0 |
| 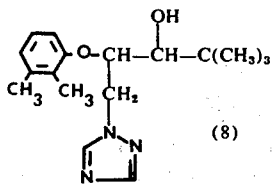 (8) | 0 |

Table B -continued

Erysiphe test/systemic

| Active compound | Infection in % of the infection of the untreated control at an active compound concentration of 100 ppm |
|---|---|
| 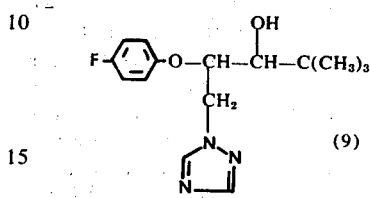 (9) | 0 |

EXAMPLE 3

Podosphaera test (powdery mildew of apples)/protective

Solvent: 4.7 parts by weight of acetone
Emulsifier: 0.3 parts by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°C and at a relative atmospheric humidity of 70%. They were then inoculated by dusting with conidia of the apple powdery mildew causative organism (*Podosphaera leucotricha*) and placed in a greenhouse at a temperature of 21° – 23°C and at a relative atmospheric humidity of about 70%.

Ten days after the inoculation, the infection of the seedlings was determined as a percentage of the untreated but also inoculated control plants.

0% means no infection: 100% means that the infection was exactly as great as in the case of the control plants.

The active compounds, the concentrations of the active compounds and the results can be seen from the following table:

Table 3

| Active compound | Podosphaera test/protective Infection in % of the infection of the untreated control at an active compound concentration of | | |
|---|---|---|---|
| | 0.01% | 0.00125% | 0.00062% |
| 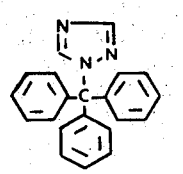 (known) (A) | 85 | — | |

Table 3 -continued

| Active compound | Podosphaera test/protective Infection in % of the infection of the untreated control at an active compound concentration of | | |
|---|---|---|---|
| | 0.01% | 0.00125% | 0.000062% |
| Cl-C₆H₃(Cl)-O-CH(CH₂-triazolyl)-CH(OH)-C(CH₃)₃ (6) | 2 | 16 | 29 |
| F-C₆H₄-O-CH(CH₂-triazolyl)-CH(OH)-C(CH₃)₃ (9) | 0 | — | — |
| C₆H₅-O-CH(CH₂-triazolyl)-CH(OH)-C(CH₃)₃ (10) | 39 | — | — |

EXAMPLE 4

Shoot treatment test/powdery mildew of cereals/protective (leaf-destructive mycosis)

To produce a suitable preparation of active compound, 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of *Erysiphe graminis var. hordei*.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of mildew infection.

The active compounds, active compound concentrations in the spray liquor and degrees of infection can be seen from the table which follows:

Table 4

| Active compound | Shoot treatment test/powdery mildew of cereals/protective Active compound concentration in the spray liquor in % by weight | Infection in % of the untreated control |
|---|---|---|
| Untreated | — | 100.0 |
| [CH₂-NH-C(=S)-S]₂Zn (known) (B) | 0.025 | 100.0 |
| | 0.01 | 100.0 |
| Triphenylmethyl-triazole (known) (A) | 0.01 | 50.0 |
| | 0.001 | 68.8 |

Table 4 -continued

| Active compound | Shoot treatment test/powdery mildew of cereals/protective Active compound concentration in the spray liquor in % by weight | Infection in % of the untreated control |
|---|---|---|
| Compound (1): 2-chloro-6-methylphenoxy derivative with OH, C(CH₃)₃, and triazolyl-CH₂ substituents | 0.01<br>0.001<br>0.0005 | 0.0<br>0.0<br>0.0 |
| Compound (6): 2,4-dichlorophenoxy derivative with OH, C(CH₃)₃, and triazolyl-CH₂ substituents | 0.01<br>0.001<br>0.0005<br>0.00025 | 3.8<br>3.8<br>16.3<br>33.8 |
| Compound (9): 4-fluorophenoxy derivative with OH, C(CH₃)₃, and triazolyl-CH₂ substituents | 0.01<br>0.001 | 25.0<br>25.0 |

EXAMPLE 5

Shoot treatment test/powdery mildew of cereals/-curative (leaf-destructive mycosis)

To produce a suitable preparation of active compound, 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test for curative activity, a procedure analogous to that used when testing for protective activity was followed, but in converse sequence. The treatment of the single-leaved young barley plants with the preparation of active compound was carried out 48 hours after the inoculation, when the infection was already manifest.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of mildew infection.

The active compounds, active compound concentrations in the spray liquor and degrees of infection can be seen from the table which follows:

Table 5

| Active compound | Shoot treatment test/powdery mildew of cereals/curative Active compound concentration in the spray liquor in % by weight | Infection in % of the untreated control |
|---|---|---|
| Untreated | — | 100.0 |
| Zn dithiocarbamate (B) (known) | 0.025 | 100.0 |
| Triphenyl-triazolyl-methane (A) (known) | 0.025<br>0.01<br>0.005 | 100.0<br>100.0<br>100.0 |

Table 5 -continued

| Active compound | Shoot treatment test/powdery mildew of cereals/curative Active compound concentration in the spray liquor in % by weight | Infection in % of the untreated control |
|---|---|---|
| 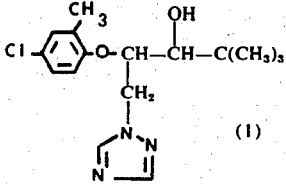 (1) | 0.01<br>0.001 | 0.0<br>0.0 |
| 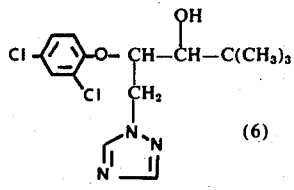 (6) | 0.01<br>0.001<br>0.005 | 0.0<br>0.0<br>41.3 |
| 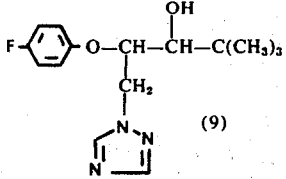 (9) | 0.1<br>0.005 | 0.0<br>0.0 |

EXAMPLE 6

Shoot treatment test/cereal rust/protective (Leaf-destructive mycosis)

To produce a suitable preparation of active compound, 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test the protective activity, one-leaved young wheat plants of the Michigan Amber variety were inoculated with a ureidospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20°C and 100% relative atmospheric humidity.

After 10 days' dwell time of the plants at a temperature of 20°C and 80–90% atmospheric humidity, the occurrence of rust pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of rust infection.

The active compounds, active compound concentrations in the spray liquor and degrees of infection can be seen from the table which follows:

Table 6

| Active compound | Shoot treatment test/cereal rust/protective Active compound concentration in the spray liquor in % by weight | Infection in % of the untreated control |
|---|---|---|
| Untreated | — | 100.0 |
| 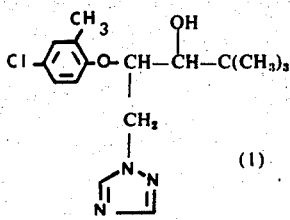 (1) | 0.025 | 18.8 |

Table 6 -continued

| Active compound | Shoot treatment test/cereal rust/protective Active compound concentration in the spray liquor in % by weight | Infection in % of the untreated control |
|---|---|---|
| (6) structure with Cl, Cl, OH, C(CH₃)₃, triazole | 0.025 | 55.0 |
| (9) structure with F, OH, C(CH₃)₃, triazole | 0.025 | 16.3 |

The process of this invention is illustrated in the following preparative Examples.

EXAMPLE 7

A. The starting material of the formula

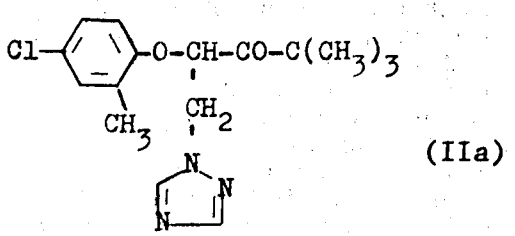

(IIa)

was prepared as follows:

Stage (a):

283 g (2 moles) of 4-chloro-2-methylphenol, 300 g of potassium carbonate and 2 g of potassium iodide were suspended in 2 l of anhydrous acetone and the suspension was heated to the boil. 359 g (2 moles) of bromopinacolone were then gradually added dropwise, while stirring, and the reaction mixture was heated for 5 hours under reflux. Thereafter, first the solvent, and then the ketone were distilled off under reduced pressure. 381 g (79% of theory) of 1-(2-methyl-4-chlorophenoxy)-3,3-dimethyl-butan-2-one of boiling point 109°–112°C/0.1 mm were obtained.

Stage (b):

144 ml (1.1 moles) of 30% strength formaldehyde solution and 8 ml of 10% strength aqueous sodium hydroxide solution were added to 145 g (0.6 mole) of 1-(4-chloro-2-methylphenoxy)-3,3-dimethyl-butan-2-one which had been dissolved in 400 ml of ethanol, and the reaction mixture was heated to the boil under reflux for 4 hours. The resulting solution was freed from the solvent under reduced pressure, the oily residue was taken up in 300 ml of ether and the mixture was extracted with three times 200 ml of water. The organic phase was dried over sodium sulfate, filtered and distilled in vacuo. After the solvent had passed over, 106 g (65% of theory) of 1-hydroxy-2-(2-methyl-4-chlorophenoxy)-4,4-dimethylpentan-3one of boiling point 122°–132°C/0.1 mm were obtained.

Stage (c):

50 g (0.42 mole) of thionyl chloride were slowly added dropwise at room temperature to a solution of 106 g (0.39 mole) of 1-hydroxy-2-(2-methyl-4-chlorophenoxy)-4,4-dimethylpentan-3-one in 400 ml of methylene chloride, while stirring and using reflux cooling, and the mixture was stirred at room temperature overnight. It was then distilled under reduced pressure. 93 g (82% of theory) of 1-chloro-2-(2-methyl-4-chlorophenoxy)-4,4-dimethyl-pentan-3-one of boiling point 113°–117°C/0.2 mm were obtained.

Stage (d):

43.4 g (0.15 mole) of 1-chloro-2-(2-methyl-4-chlorophenoxy)-4,4-dimethyl-pentan-3-one and 21.4 g (0.15 mole) of potassium carbonate were suspended in 300 ml of anhydrous acetone and 20.7 g (0.3 mole) of 1,2,4-triazole were added dropwise thereto at the boil, while stirring. After boiling for 20 hours under reflux, the precipitate was filtered off, well rinsed with ether and discarded. The filtrate was freed from the solvent in vacuo, the oily residue was dissolved in 300 ml of ether and the solution was twice extracted with 200 ml of water to remove the excess triazole. The organic phase was dried over sodium sulfate, filtered and freed from the solvent in vacuo. The residue crystallized after trituration with pentane. 30 g (62% of theory) of 1-[1,2,4-triazolyl-(1)]-2-(2-methyl-4-chlorophenoxy)-4,4-dimethyl-pentan-3-one of melting point 63°–65°C were obtained.

(B)

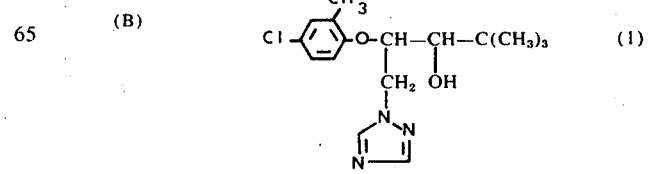

(1)

9.65 g (0.03 mole) of 1-[1,2,4-triazolyl-(1)]-2-(2-methyl-4-chlorophenoxy)-4,4-dimethyl-pentan-3-one were dissolved in 100 ml of methanol and 2 g (0.05 mole) of sodium borohydride were added thereto in portions at 5° to 10°C. After stirring for 15 hours at room temperature, 10 ml of concentrated hydrochloric acid were added and the resulting suspension was stirred into 250 ml of saturated sodium bicarbonate solution. The resulting precipitate was filtered off, rinsed with 50 ml of water and dried. 9.1 g (94% of theory) of 1-[1,2,4-triazolyl-(1)]-2-(2-methyl-4-chlorophenoxy)-4,4-dimethyl-pentan-3-ol of melting point 124°–126°C were obtained.

EXAMPLE 8

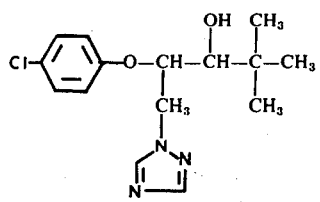 (2)

6.2 g (0.02 mole) of 1-[1,2,4-triazolyl-(1)]-2(4-chlorophenoxy)-4,4-dimethyl-pentan-3-one were dissolved in 60 ml of ethanol and a sodium hydroxide solution containing 1.6 g (0.04 mole) of sodium hydroxide in 8 ml of water was added thereto, followed by 6.5 g (0.06 mole) of formamidinesulfinic acid. The reaction mixture was heated to the boil under reflux for 3 hours and filtered, and the solvent was distilled off in vacuo. The oily residue was taken up in 50 ml of water and twice extracted with 50 ml of methylene chloride. The combined organic phases were twice washed with 50 ml of water, dried over sodium sulfate and freed from the solvent in vacuo. The resulting oil was boiled up with petroleum ether, whereupon it crystallised. Filtration gave 5 g (80% of theory) of 1-[1,2,4-triazolyl-(1)]-2-(4-chlorophenoxy)-4,4-dimethylpentan-3-ol of melting point 103°C.

EXAMPLE 9

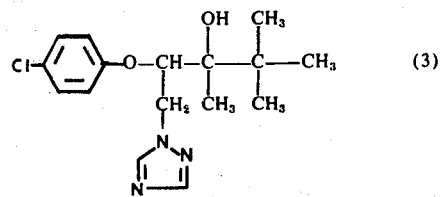 (3)

A solution of 31.2 g (0.22 mole) of methyl iodide in 100 ml of anhydrous ether was added dropwise to a suspension of 5.35 g (0.22 mole) of magnesium filings in 50 ml of anhydrous ether, while stirring and using reflux cooling, the solvent coming to the boil during the addition. After completion of the addition, a solution of 30.8 g (0.1 mole) of 1-[1,2,4-triazolyl-(1)]-2-(4-chlorophenoxy)-4,4-dimethyl-pentan-3-one in 100 ml of anhydrous ether was added dropwise to this Grignard solution, and the whole was heated to the boil under reflux for 18 hours. After cooling, the reaction mixture was introduced into a solution of 80 g of ammonium chloride in 600 ml of water, 250 ml of ethyl acetate were added, and the mixture was stirred for 15 minutes. The organic phase was separated off and the aqueous phase was again extracted with ethyl acetate. Both ethyl acetate extracts were washed with twice 100 ml of water, dried over sodium sulfate and freed from the solvent in vacuo. The crystalline precipitate was taken up in hot petroleum ether, which left the precipitate undissolved, and was filtered off hot. 25 g (77% of theory) of 1-[1,2,4-triazolyl-(1)]-2-(4-chlorophenoxy)-3,4,4-trimethyl-pentan-3-ol of melting point 150°C were obtained.

The compounds of the general formula

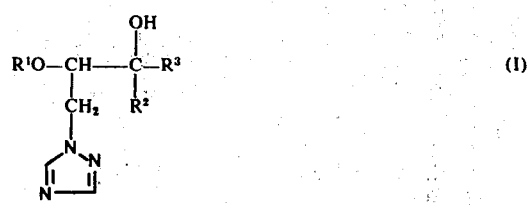 (I)

which are listed below were obtained by methods analogous to those described in Examples 7 to 9:

| Compound No. | R¹ | R² | R³ | Melting point °C |
|---|---|---|---|---|
| 4 | 4-Cl-C₆H₄ | H | C(CH₃)₃ | 106–108 |
| 5 | 3-Cl-C₆H₄ | H | C(CH₃)₃ | 131–133 |
| 6 | 2,4-Cl₂-C₆H₃ | H | C(CH₃)₃ | 115 |
| 7 | 2,5-Cl₂-C₆H₃ | H | C(CH₃)₃ | 165–167 |

-continued

| Compound No. | R¹ | R² | R³ | Melting point °C |
|---|---|---|---|---|
| 8 | 2,6-dimethylphenyl | H | C(CH₃)₃ | 132–134 |
| 9 | 4-fluorophenyl | H | C(CH₃)₃ | 121–122 |
| 10 | phenyl | H | C(CH₃)₃ | 129 |
| 11 | 4-fluorophenyl | CH₃ | C(CH₃)₃ | 160–164 |
| 12 | 4-fluorophenyl | –CH₂–phenyl | C(CH₃)₃ | 152–155 |
| 13 | phenyl | phenyl | H | 118–119 |
| 14 | 4-chlorophenyl | phenyl | H | 94–98 |
| 15 | 4-chlorophenyl | 4-chlorophenyl | H | 134–135 |
| 16 | 2,4-dichlorophenyl | 4-chlorophenyl | H | 132–135 |

Other compounds which can be similarly prepared include:

1-[1,2,4-triazolyl-(1)]-2-(α-naphthoxy)-3,3-dicyclohexyl-propan-3-ol,

1-[1,2,4-triazolyl-(1)]-2-(6-methyl-β-naphthoxy)-3-allyl-pentan-3-ol,

1-[1,2,4-triazolyl-(1)]-2-phenoxy-3-p-chlorobenzyl-heptan-3-ol,

1-[1,2,4-triazolyl-(1)]-2-phenoxy-3-phenyl-4-methylpentan-3-ol,

1-[1,2,4-triazolyl-(1)]-2-phenoxy-3-p-fluorophenyl-3-cyclopentyl-propan-3-ol,

1-[1,2,4-triazolyl-(1)]-3-phenoxy-3-m-isopropylphenyl-4,4-dimethyl-pentan-3-ol,

1-[1,2,4-triazolyl-(1)]-2-phenoxy-3-o-ethoxyphenethyl-4,4-dimethyl-pentan-3-ol, and the like.

It will be appreciated that the instant specification and examples are set forth by way of illustration and not limitation, and that various modifications and changes may be made without departing from the spirit and scope of the present invention.

What is claimed is:

1. A 1-[1,2,4-triazolyl-(1)]-2-aryloxy-3-hydroxyalkane of the formula

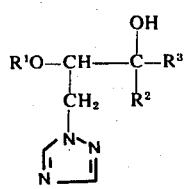

in which $R^1$ is optionally monosubstituted or polysubstituted phenyl or naphthyl, the substituents being selected from halogen, straight-chain or branched alkyl with 1 to 6 carbon atoms, alkoxy, alkylthio and alkylsulfonyl with 1 to 4 carbon atoms, halogenoalkyl with 1 or 2 carbon atoms and 1 to 5 halogen atoms, halogenoalkoxy and halogenoalkylthio with 1 or 2 carbon atoms and 3 to 5 halogen atoms, alkoxycarbonyl with 1 to 4 carbon atoms in the alkoxy moiety, phenyl in the o - or p - position, amino and nitro, $R^2$ is hydrogen; alkyl with up to 6 carbon atoms; optionally substituted phenyl or naphthyl or phenalkyl or naphthalkyl with 1 or 2 carbon atoms in the alkyl moiety, substituents on the phenyl or naphthyl radicals being selected from fluorine, chlorine, alkyl with up to 4 carbon atoms and alkoxy with up to 4 carbon atoms; allyl or cyclohexyl, and $R^3$ is straight-chain or branched alkyl with 1 to 6 carbon atoms, or cycloalkyl with 5 to 7 carbon atoms, or can be hydrogen if $R^2$ does not denote hydrogen, or a salt thereof with fungicidal activity.

2. The compound according to claim 1 wherein such compound is 1-[1,2,4-triazolyl-(1)]-2-(2,4-dichlorophenoxy)-4,4-dimethyl-pentan-3-ol of the formula

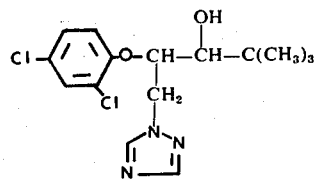

or a salt thereof with fungicidal activity.

3. The compound according to claim 1 wherein such compound is 1-[1,2,4-triazolyl-(1)]-2-(2,5-dichlorophenoxy)-4,4-dimethyl-pentan-3-ol of the formula

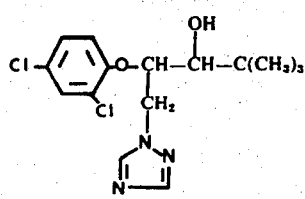

or a salt thereof with fungicidal activity.

4. The compound according to claim 1 wherein such compound is 1-[1,2,4-triazolyl-(1)]-2-(2,3-dimethylphenoxy)-4,4-dimethyl-pentan-3-ol of the formula

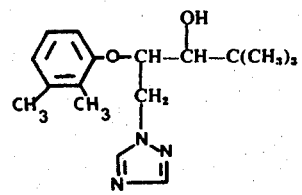

or a salt thereof with fungicidal activity.

5. The compound according to claim 1 wherein such compound is 1-[1,2,4-triazolyl-(1)]-2-(4-fluorophenoxy)-4,4-dimethyl-pentan-3-ol of the formula

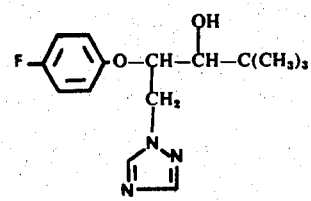

or a salt thereof with fungicidal activity.

* * * * *